(12) United States Patent
Inoue

(10) Patent No.: US 12,038,391 B2
(45) Date of Patent: Jul. 16, 2024

(54) OBSERVATION DEVICE, AND OBSERVATION METHOD

(71) Applicant: Furuno Electric Co., Ltd., Hyogo (JP)

(72) Inventor: Shuhei Inoue, Nishinomiya (JP)

(73) Assignee: Furuno Electric Co., Ltd., Nishinomiya (JP)

(*) Notice: Subject to any disclaimer, the term of this patent is extended or adjusted under 35 U.S.C. 154(b) by 438 days.

(21) Appl. No.: 17/453,142

(22) Filed: Nov. 1, 2021

(65) Prior Publication Data
US 2022/0050063 A1  Feb. 17, 2022

Related U.S. Application Data

(63) Continuation of application No. PCT/JP2020/016417, filed on Apr. 14, 2020.

(30) Foreign Application Priority Data

May 14, 2019 (JP) ................ 2019-091266

(51) Int. Cl.
*G01N 22/00* (2006.01)
*G01N 33/18* (2006.01)

(52) U.S. Cl.
CPC ............ *G01N 22/00* (2013.01); *G01N 33/18* (2013.01)

(58) Field of Classification Search
CPC ........ G01N 22/00; G01N 33/18; G01N 22/04; G01S 13/95; G01W 1/00
See application file for complete search history.

(56) References Cited

U.S. PATENT DOCUMENTS

| | | | |
|---|---|---|---|
| 6,411,430 B1 * | 6/2002 | Ogino | H04B 10/2941 359/337.13 |
| 2007/0164737 A1 | 7/2007 | Pusiol | |
| 2020/0257020 A1 * | 8/2020 | Spatzierer | G01W 1/02 |

FOREIGN PATENT DOCUMENTS

| | | |
|---|---|---|
| CN | 105548975 A | 5/2016 |
| JP | S55165277 U | 11/1980 |
| JP | H083505 B2 | 1/1996 |

(Continued)

OTHER PUBLICATIONS

Capsoni, C. et al., "Radiometer-based calibration of the relation between radar reflectivity and microwave attenuation," Radio Science, vol. 38, No. 3, Apr. 19, 2003, 8 pages.

(Continued)

*Primary Examiner* — Xin Y Zhong
(74) *Attorney, Agent, or Firm* — Alleman Hall & Tuttle LLP

(57) ABSTRACT

An observation device includes a mixer, a detector, a variable attenuator, a calibration information setting module, and an observation data generating module. The mixer mixes an RF signal of an observation object with a local signal to generate an IF signal. The detector detects the IF signal to generate a detection signal. The variable attenuator is connected between the mixer and the detector to attenuate the IF signal. The calibration information setting module sets calibration information from a change of intensity of the detection signal according to a value of the variable attenuator. The observation data generator generates observation data of the RF signal by using the intensity of the detection signal obtained in a state where the value of the variable attenuator is fixed and the calibration information.

13 Claims, 8 Drawing Sheets

(56) References Cited

FOREIGN PATENT DOCUMENTS

| | | |
|---|---|---|
| JP | 2681997 B2 | 11/1997 |
| JP | H11264736 A | 9/1999 |
| JP | 2013224884 A | 10/2013 |

OTHER PUBLICATIONS

China National Intellectual Property Administration, Office Action and Search Report Issued in Application No. 202080027533.2, Nov. 16, 2023, 22 pages.
Chattopadhray, R. et al., "Improved Automation of Mixer Loss Measurements," Foreign Metrology, vol. 3, Dec. 31, 1987, 2 pages. This reference was cited in a Chinese office action dated Nov. 16, 2023 in a corresponding patent application.
European Patent Office, Extended European Search Report Issued in Application No. 20806406.3, Dec. 12, 2022, Germany, 9 pages.
Li, S. et al., "Terahertz Superconducting Radiometric Spectrometer in Tibet for Atmospheric Science," International Journal of Infrared and Millimeter Waves, vol. 40, No. 2, Dec. 17, 2018, 12 pages.
ISA Japan Patent Office, International Search Report Issued in Application No. PCT/JP2020/016417, Jul. 21, 2020, WIPO, 4 pages.

\* cited by examiner

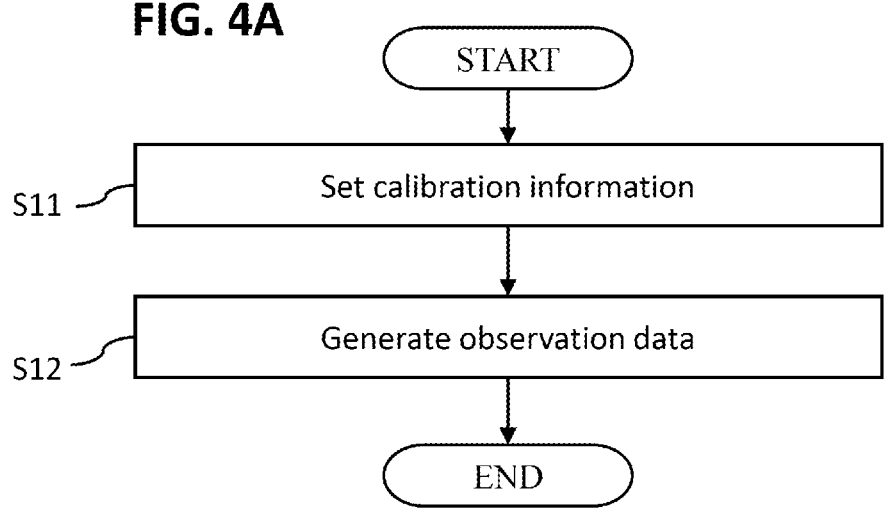
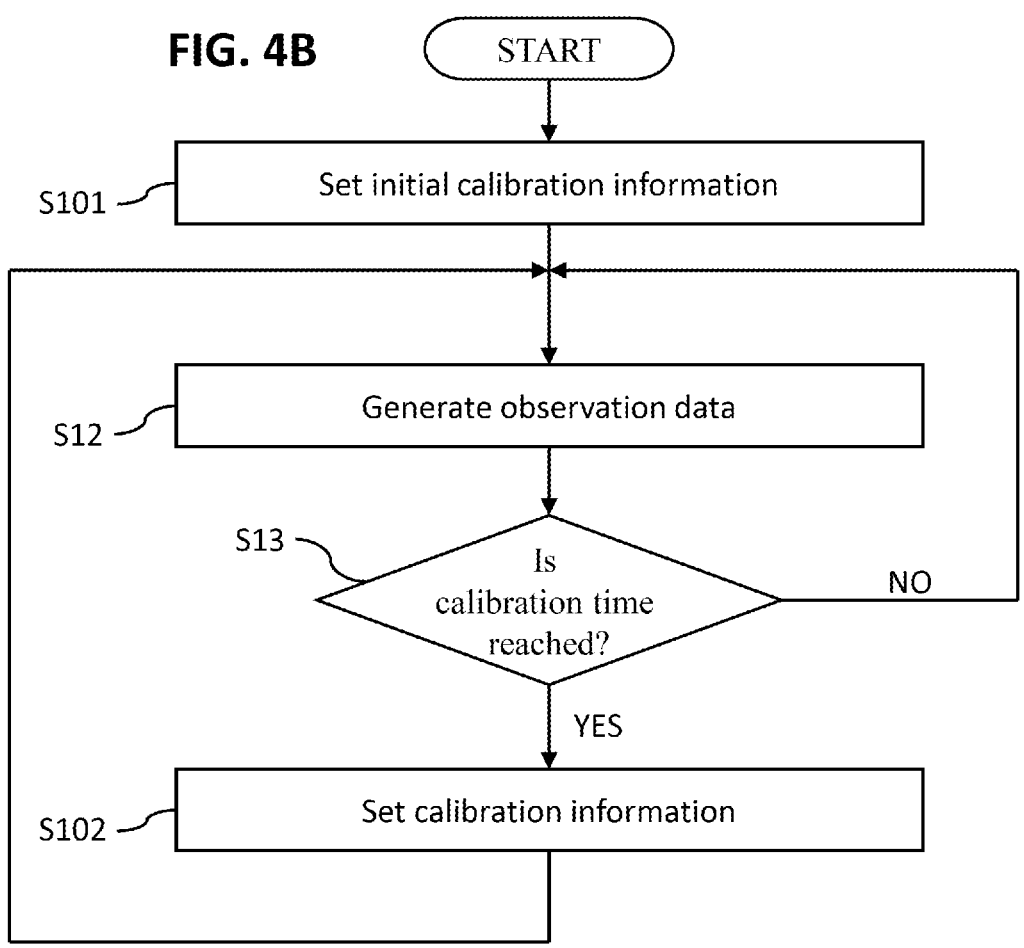

OBSERVATION DEVICE, AND OBSERVATION METHOD

CROSS-REFERENCE TO RELATED APPLICATION(S)

This application is a continuation of PCT International Application No. PCT/JP2020/016417, which was filed on Apr. 14, 2020, and which claims priority to Japanese Patent Application Ser. No. 2019-091266 filed on May 14, 2019, the entire disclosures of each of which are herein incorporated by reference for all purposes.

TECHNICAL FIELD

The present invention relates to a technique for observing a specific radio frequency (RF) signal such as a radiated electromagnetic wave generated by water vapor.

BACKGROUND

Conventionally, an observation device for water vapor is known.

SUMMARY

One method of observing water vapor is to use an intensity of radiated electromagnetic waves (RF signals). In this case, there is a problem that the observation result has an error due to the characteristics of circuit elements constituting the observation device such as a detector.

Accordingly, it is an object of the present invention to provide an observation technique capable of reducing errors in observation results.

An observation device includes: a mixer configured to mix a radio frequency (RF) signal and a local signal of an observation object, and to generate an intermediate frequency (IF) signal; a detector configured to detect the IF signal, and to generate a detection signal; a variable attenuator, connected between the mixer and the detector, configured to attenuate the IF signal; and processing circuitry configured to: set calibration information from a relationship between a change in a value of the variable attenuator and a change in an intensity of the detection signal.

The observation device further comprising: the processing circuitry is further configured to: generate observation data of the RF signal by using the intensity of the detection signal obtained in a state where the value of the variable attenuator is fixed and the calibration information.

The observation device further comprising: an IF filter connected between the mixer and the detector; and an amplifier connected between the IF filter and the detector; wherein the variable attenuator is located between the mixer and the amplifier.

In this configuration, the calibration information is obtained by measuring a level of the detection signal while changing the value of the variable attenuator. Therefore, the calibration information can be obtained with a simple configuration and processing. An error caused by the detector at the time of observation to the phenomenon of the observation object is calibrated by the calibration information.

According to the present invention, the error of the observation result can be reduced.

BRIEF DESCRIPTION OF THE DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as claimed herein:

FIG. 4A is a flow chart showing a first mode of the main process executed by the observation device, and FIG. 4B is a flow chart showing a second mode of the main process executed by the observation device;

DETAILED DESCRIPTION

Figure 1:
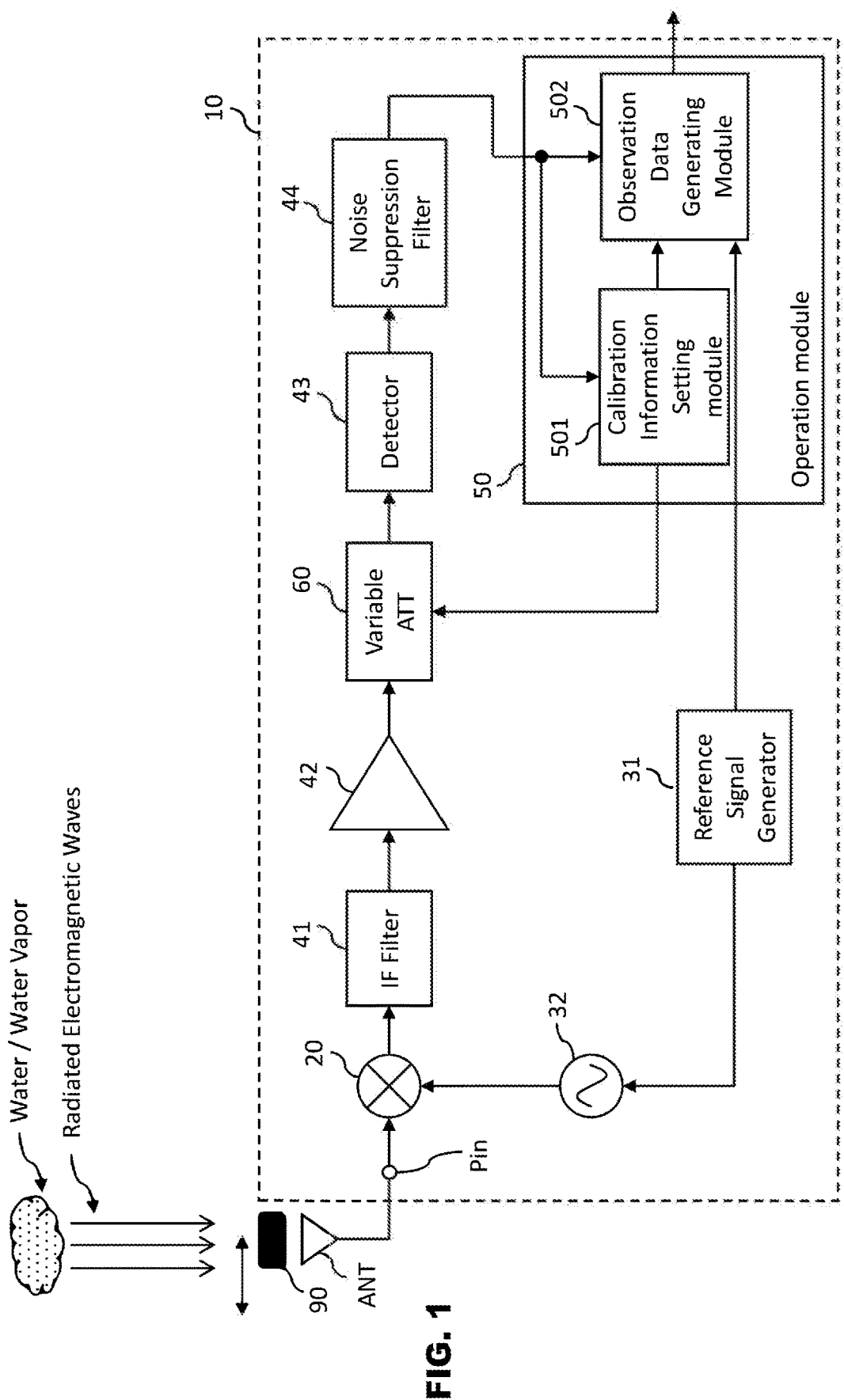
FIG. 1 is a block diagram showing a configuration of an observation device according to a first embodiment.

An observation technique according to a first embodiment of the present invention will be described with reference to the drawings. FIG. 1 is a block diagram showing a configuration of an observation device 10 according to a first embodiment. Note that the observation techniques shown in the following embodiments are used for the observation of water vapor. However, the configuration of the observation device 10 according to the present embodiment can be applied to a device for observing a radio frequency (RF) signal such as an electromagnetic wave emitted to an observation object.

As shown in FIG. 1, the observation device 10 includes a mixer 20, a reference signal generator 31, a local signal generator 32, an intermediate frequency (IF) filter 41, an amplifier 42, a detector 43, a noise suppression filter 44, an operation module 50, and a variable attenuator (variable ATT) 60. The calculation module 50 includes a calibration information setting module 501 and an observation data generating module 502.

The mixer 20, the local signal generator 32, the IF filter 41, the amplifier 42, the detector 43, the noise suppression filter 44, and the variable attenuator (variable ATT) 60 can be realized, for example, by a predetermined analog electronic circuit. The reference signal generator 31 and the operation module 50 can be realized by, for example, an arithmetic element such as a CPU and a program executed by the arithmetic element.

The observation device 10 has an input terminal Pin. The input terminal Pin is connected to an antenna ANT via a first stage low noise amplifier (LNA) (not shown). The input terminal Pin is connected to the mixer 20. In this case, the mixer 20 is directly connected to the first stage LNA. The local signal generator 32 is connected to the mixer 20. The local signal generator 32 is connected to a reference signal generator 31. The reference signal generator 31 is connected to the calculation module 50.

The mixer 20 is connected to the IF filter 41, and the IF filter 41 is connected to the amplifier 42. The amplifier 42 is connected to the variable attenuator 60, and the variable attenuator 60 is connected to the detector 43. The detector 43 is connected to a noise suppression filter 44, and the noise suppression filter 44 is connected to the operation module 50.

The antenna ANT receives an electromagnetic wave radiated from a black radiator (black body) 90 or an electromagnetic wave radiated from water vapor to be observed. The RF signal (electromagnetic wave) received by the antenna ANT is inputted to the input terminal Pin via the first stage LNA.

The RF signal input to the input terminal Pin is input to the mixer 20.

The reference signal generator 31 generates, for example, a reference signal composed of sawtooth waves. The reference signal generator 31 outputs the reference signal to the local signal generator 32 and the operation module 50.

The local signal generator 32 generates a local signal of a predetermined frequency based on the reference signal. A frequency of the local signal is set within a frequency range of a frequency spectrum of an observation object. The local signal generator 32 individually generates local signals of a plurality of frequencies. In other words, the local signal generator 32 generates the local signals of the plurality of frequencies at different timings. The local signal generator 32 outputs the local signal to the mixer 20.

The mixer 20 mixes the RF signal and the local signal to down-convert them to generate an IF signal. The mixer 20 outputs the IF signal to the IF filter 41.

The IF filter 41 has filter characteristics including a frequency necessary for generating observation data of the observation object in a pass region and other noise components in an attenuation region. The IF filter 41 filters the IF signal and outputs it to the amplifier 42.

The amplifier 42 amplifies the IF signal and outputs it to the variable attenuator 60.

The variable attenuator 60 has a circuit configuration capable of adjusting an attenuation of the IF signal. An attenuation of the variable attenuator 60 can be set, for example, by the calibration information setting module 501 of the operation module 50. The IF signal that has passed through the variable attenuator 60 is input to the detector 43.

The detector 43 detects the IF signal and outputs a detection signal.

The noise suppression filter 44 is realized by, for example, a smoothing filter. The noise suppression filter 44 suppresses a noise component of the detection signal and outputs it to the operation module 50.

The calibration information setting module 501, which will be described later in detail, sets calibration information for calibrating errors caused by the circuits up to the detector 43 including the detector 43. The calibration information setting module 501 outputs the calibration information to the observation data generating module 502.

The observation data generating module 502 generates the observation data by using a detection signal (reference detection signal) obtained in a state where the blackbody 90 covers a reception surface of the antenna ANT and a detection signal (observation object detection signal) obtained in a state where the blackbody 90 is removed from the reception surface of the antenna ANT. In this case, the reference detection signal and the observation object detection signal are obtained in a state where the attenuation of the variable attenuator 60 is fixed.

More specifically, the observation data generating module 502 receives the reference detection signal and the observation object detection signal in a state where the attenuation of the variable attenuator 60 is fixed. The observation data generating module 502 generates the observation data from a difference (intensity difference) between an intensity of the reference detection signal and an intensity of the observation object detection signal.

The observation data generating module 502 calculates an intensity difference for each of a plurality of frequency components of the RF signal. Thus, the observation data generating module 502 obtains the frequency spectrum of the radiated electromagnetic wave for the phenomenon to be observed as the observation data.

At this time, the observation data generating module 502 performs calibration in advance using the calibration information. Thus, errors due to the detector 43 and the like included in the intensity difference are suppressed. Therefore, the observation data becomes a highly accurate value (value with little error) corresponding to the intensity of the radiation electromagnetic wave of the observation object.

The detector 43 generally has, for example, a temperature characteristic. Note that, although circuit elements (electronic devices) other than the detector 43 also have temperature characteristics, in the present application, the detector 43, which has a large influence on the output due to the temperature characteristics, will be mainly described. Accordingly, the intensity of the detection signal varies depending on a temperature of the detector 43, for example, an environmental temperature of the observation device 10. As described above, when the intensity of the detection signal changes depending on the environmental temperature, an error occurs in the observation data. Therefore, the observation device 10 sets the calibration information according to the following concept and uses it for the generation of the observation data.

Figure 2A:
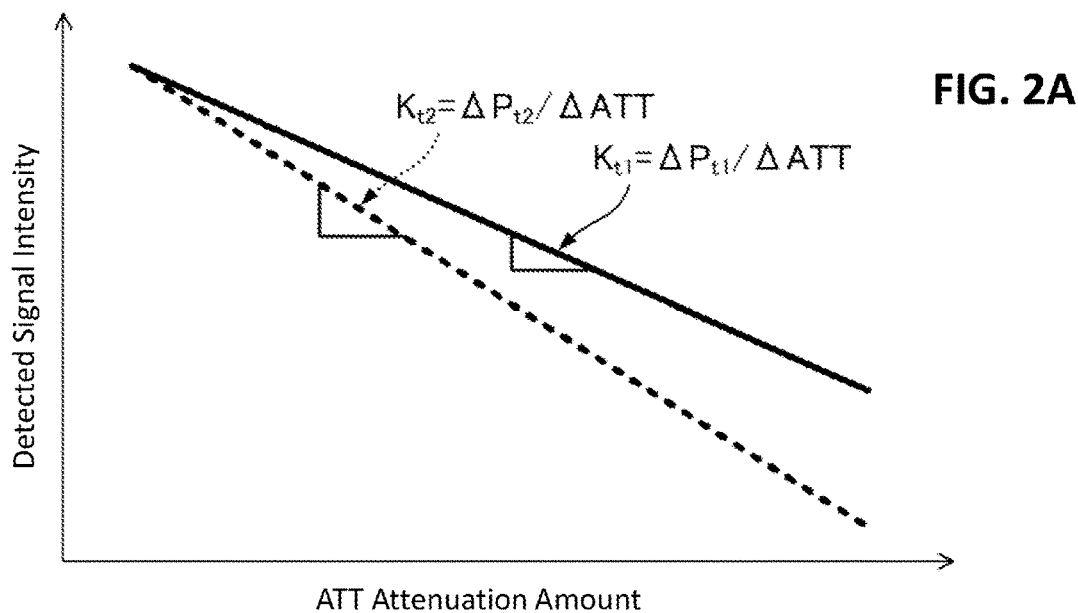
FIG. 2A is a graph showing a relationship between an intensity of a detected signal and an attenuation amount.
Figure 2B:
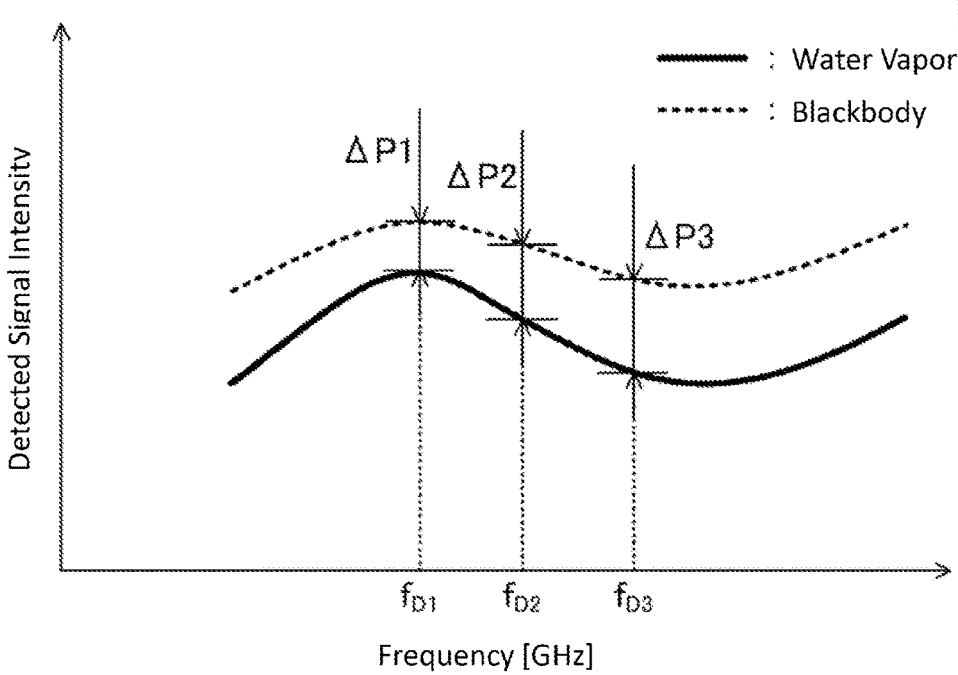
FIG. 2B is a graph showing a definition of an intensity difference.

FIG. 2A is a graph showing a relationship between the intensity of the detected signal and an attenuation amount, and FIG. 2B is a graph showing the definition of the intensity difference.

The calibration information is set, for example, in a state where the blackbody 90 covers the receiving surface of the antenna ANT. It should be noted that the blackbody 90 need not be used as long as the environment in which an RF signal having a constant signal intensity is input to the antenna ANT can be maintained.

The calibration information setting module 501 generates a control signal for changing the attenuation to the variable attenuator 60. The variable attenuator 60 changes the attenuation amount according to the control signal. Thus, the variable attenuator 60 attenuates and outputs the IF signal with the set attenuation amount.

The calibration information setting module 501 adjusts the attenuation of the variable attenuator 60 and acquires an intensity of the detection signal for the plurality of attenuation amounts. The set attenuation amount is set within a range necessary for generation of the observation data, and the number of set attenuation amount can be appropriately set.

The calibration information setting module 501 calculates an amount of change $\Delta Pt$ of the intensity of the detection signal with respect to an amount of change $\Delta ATT$ of the attenuation of the variable attenuator 60, as shown in FIG. 2A, from the relationship between the difference of the plurality of attenuation amounts and the difference of the intensity of the detection signal with respect to each attenuation amount. In this case, the calibration information setting module 501 may calculate the amount of change ΔPt by calculating an average value or the like by using a plurality of sets of the difference between the plurality of attenuation amounts and the difference in intensity of the detection signal with respect to each attenuation amount.

As described above, the detector 43 and the like have a temperature characteristic. Therefore, as shown in FIG. 2A, an amount of change ΔPt1 (a rate of change Kt1 of the signal intensity) of the detected signal intensity at a temperature t1 with respect to the amount of change ΔATT of the attenuation of the variable attenuator 60 at the temperature t1 is different from an amount of change ΔPt2 (a rate of change Kt2 of the signal intensity) of the detected signal intensity at a temperature t2 with respect to the amount of change ΔATT of the attenuation of the variable attenuator 60 at the temperature t2.

The calibration information setting module 501 calculates a rate of change Kt of the intensity depending on the temperature. Then, the calibration information setting module 501 calculates the calibration information, for example, by using the rate of change Kt as the calibration information or by using the rate of change Kt.

Thus, the calibration information appropriately reflects the temperature characteristic of the detector 43 or the like.

The observation data generating module 502 generates the observation data from the difference (intensity difference) between the intensity of the reference detection signal and the intensity of the observation object detection signal, as described above. The observation data generating module 502 generates the observation data from, for example, an intensity difference ΔP1, an intensity difference ΔP2, and an intensity difference ΔP3 shown in FIG. 2B. That is, the observation data generating module 502 generates the observation data from the intensity difference between the detection signals in the two different states.

Therefore, by using the rate of change Kt of the intensity as the calibration information, the observation data generating module 502 can accurately calibrate the intensity difference of the detection signal, and can generate a highly accurate observation data. For example, the observation data generating module 502 normalizes the intensity difference between the reference detection signal and the observation object detection signal by using the rate of change Kt. Thus, the observation data generating module 502 can suppress an error caused by the temperature characteristic or the like of the detector 43 and generate a high-precision observation data.

In the present embodiment, the two different states are a state in which radiated electromagnetic waves are received from the blackbody 90 and a state in which radiated electromagnetic waves are received from water vapor. Therefore, the observation device 10 can generate the observation data corresponding to the intensity of the radiation electromagnetic wave of water vapor with high accuracy.

As described above, by using the configuration of this embodiment, the observation device 10 can generate an observation data of a phenomenon to be observed, such as water vapor, with high accuracy. The observation device 10 can set calibration information only by generating a detection signal while adjusting the attenuation using the variable attenuator 60. That is, the observation device 10 can set the calibration information with a simple configuration and simple processing, and can generate a highly accurate observation data.

Figure 3:
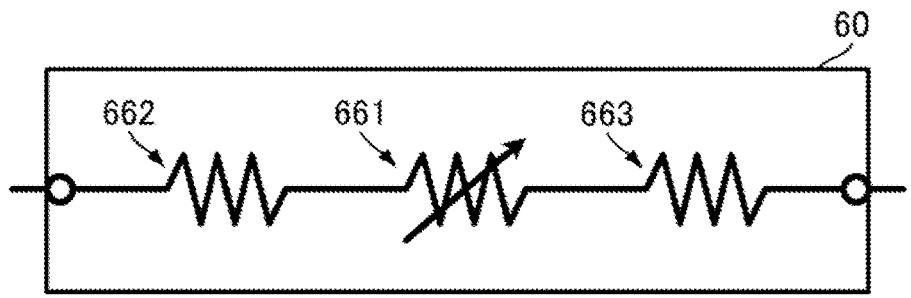
FIG. 3 is an equivalent circuit diagram showing an example of a circuit configuration of a variable attenuator.

FIG. 3 is an equivalent circuit diagram showing an example of the circuit configuration of the variable attenuator 60. As shown in FIG. 3, the variable attenuator 60 includes a variable impedance circuit 661, a fixed resistance circuit 662, and a fixed resistance circuit 663. The fixed resistance circuit 662 corresponds to the "first fixed resistance circuit" of the present invention, and the fixed resistance circuit 663 corresponds to the "second fixed resistance circuit" of the present invention.

The variable impedance circuit 661, the fixed resistance circuit 662, and the fixed resistance circuit 663 are connected in series. At this time, the variable impedance circuit 661 is connected between the fixed resistance circuit 662 and the fixed resistance circuit 663. The fixed resistance circuit 662 is connected to the output terminal of the amplifier 42, and the fixed resistance circuit 663 is connected to the detector 43.

The variable impedance circuit 661 is a circuit including a resistance element and a semiconductor element, and changes impedance (resistance value) by a control signal flowing in the semiconductor element.

The fixed resistance circuit 662 and the fixed resistance circuit 663 have, for example, a circuit configuration in which a plurality of resistance elements are connected in a predetermined pattern. The fixed resistance circuit 662 functions as an impedance matching circuit between the variable impedance circuit 661 and the amplifier 42. The fixed resistance circuit 663 functions as an impedance matching circuit between the variable impedance circuit 661 and the detector 43. Thus, even if the impedance of the variable impedance circuit 661 is changed, the change and mismatch of the impedance between the variable attenuator 60 and the amplifier 42 can be suppressed, and the change and mismatch of the impedance between the variable attenuator 60 and the detector 43 can be suppressed. Therefore, the observation device 10 can obtain highly accurate calibration information and generate a highly accurate observation data.

In the above description, the setting process of the calibration information and the generation process of the observation data are shown to be realized by the respective functional parts, but each of the above-mentioned processes may be stored as a program, and the above-mentioned functions of the observation device 10 may be realized by executing the program by a computing device such as a computer. The specific contents of the respective processes are described above, and the explanation thereof is omitted except for portions where additional explanation is considered necessary.

FIG. 4A is a flow chart showing a first mode of the main process executed by the observation device 10, and FIG. 4B is a flow chart showing a second mode of the main process executed by the observation device 10.

In the processing of FIG. 4A, a computing device constituting the observation device 10 sets calibration information (S11). An arithmetic module generates an observation data by using the calibration information (S12). This processing shows a case where the calibration information is set and used at the beginning of observation. This method may be used when the observation time is short.

In the processing of FIG. 4B, the arithmetic module sets initial calibration information (S101). The arithmetic module generates an observation data by using the initial calibration information (S12). The arithmetic module has a time counting function and repeats the process of generating the observation data by using the initial calibration information (S12) until a calibration time is reached (S13: NO).

When the calibration time is reached (S 13: YES), the arithmetic module sets new calibration information (S102). Then, the arithmetic module performs calibration by using the updated calibration information, and generates the observation data (S12). By using such processing, the arithmetic module can periodically update the calibration information while continuously generating the observation data. The update of the calibration information is not limited to that based on the time, and may be performed, for example, when the level (intensity) of the electromagnetic wave of the blackbody 90 exceeds a preset reference value.

Therefore, the arithmetic module can continuously generate a high-precision observation data. In addition, since the temperature change of the detector is generally not rapid, by updating the calibration information at predetermined intervals, the arithmetic module can continuously generate the high-precision observation data while reducing the processing load.

Figure 5:
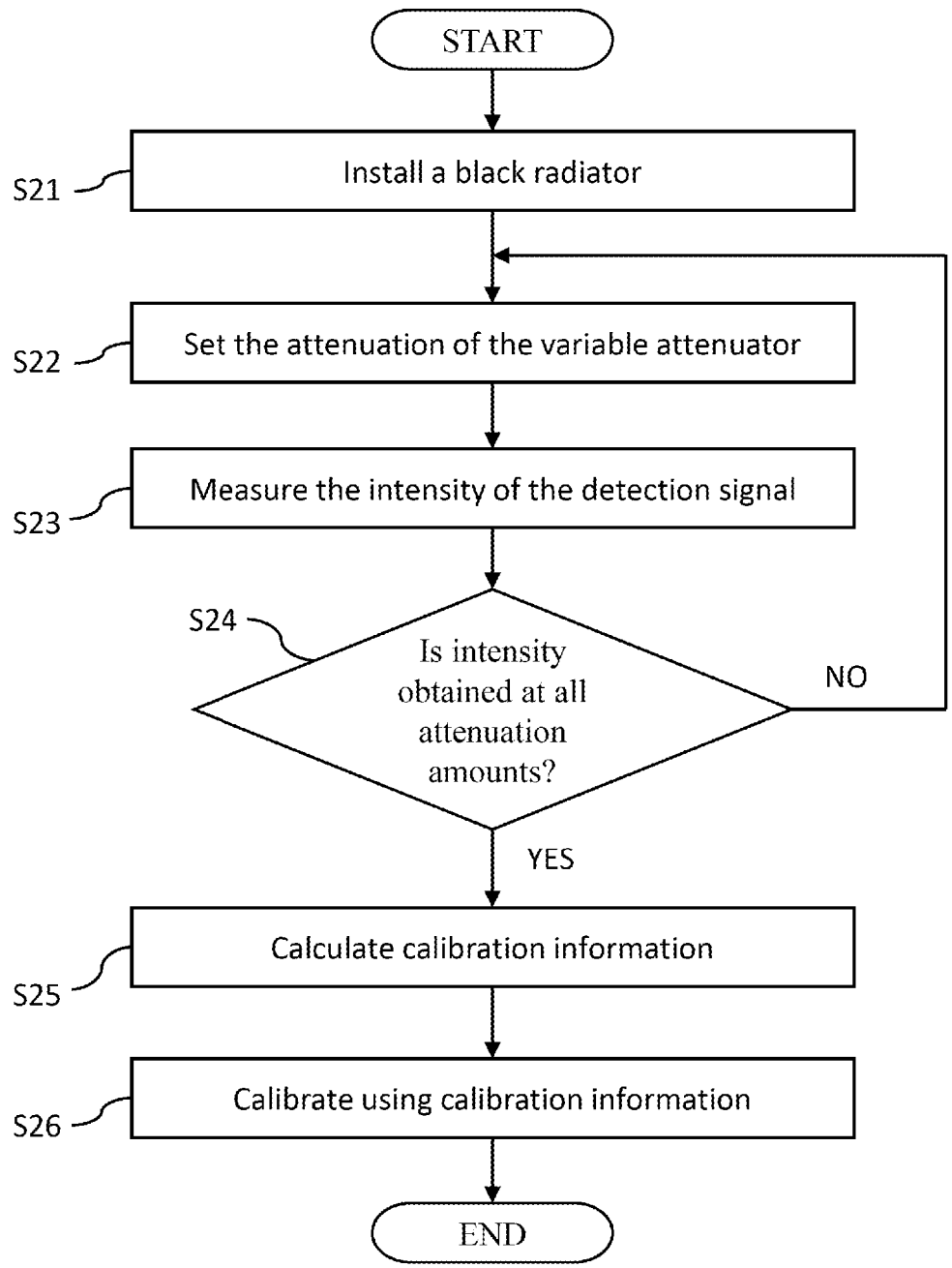
FIG. 5 is a flow chart illustrating an example of a specific method for setting calibration information.

FIG. 5 is a flow chart showing an example of a specific method of setting calibration information. As shown in FIG. 5, the blackbody 90 is installed on the receiving surface of the antenna ANT (S21). The arrangement of the blackbody 90 may be mechanically controlled by providing a moving mechanism for the blackbody 90 on the antenna ANT or manually. The arithmetic module sets the attenuation of the variable attenuator 60 (S22). The arithmetic module measures the intensity of the detection signal obtained by the set attenuation amount of the variable attenuator 60 (S23).

The arithmetic module preliminarily sets the range of all attenuation amounts for obtaining the intensity difference necessary for generating the observation data. If the intensity of the detection signal is not obtained in all attenuation amounts (S24: NO), the arithmetic module changes the attenuation setting of the variable attenuator 60 (S22), and measures the intensity of the detection signal (S23).

When the detection signal is obtained for the whole range of attenuation amounts (S24: YES), the arithmetic module calculates the calibration information from the difference in the intensity of the detection signal in the different attenuation amounts, that is, the rate of change of the intensity (S25). Using the calibration information, the arithmetic module performs calibration for the measurement of the intensity described later (S26).

Figure 6:
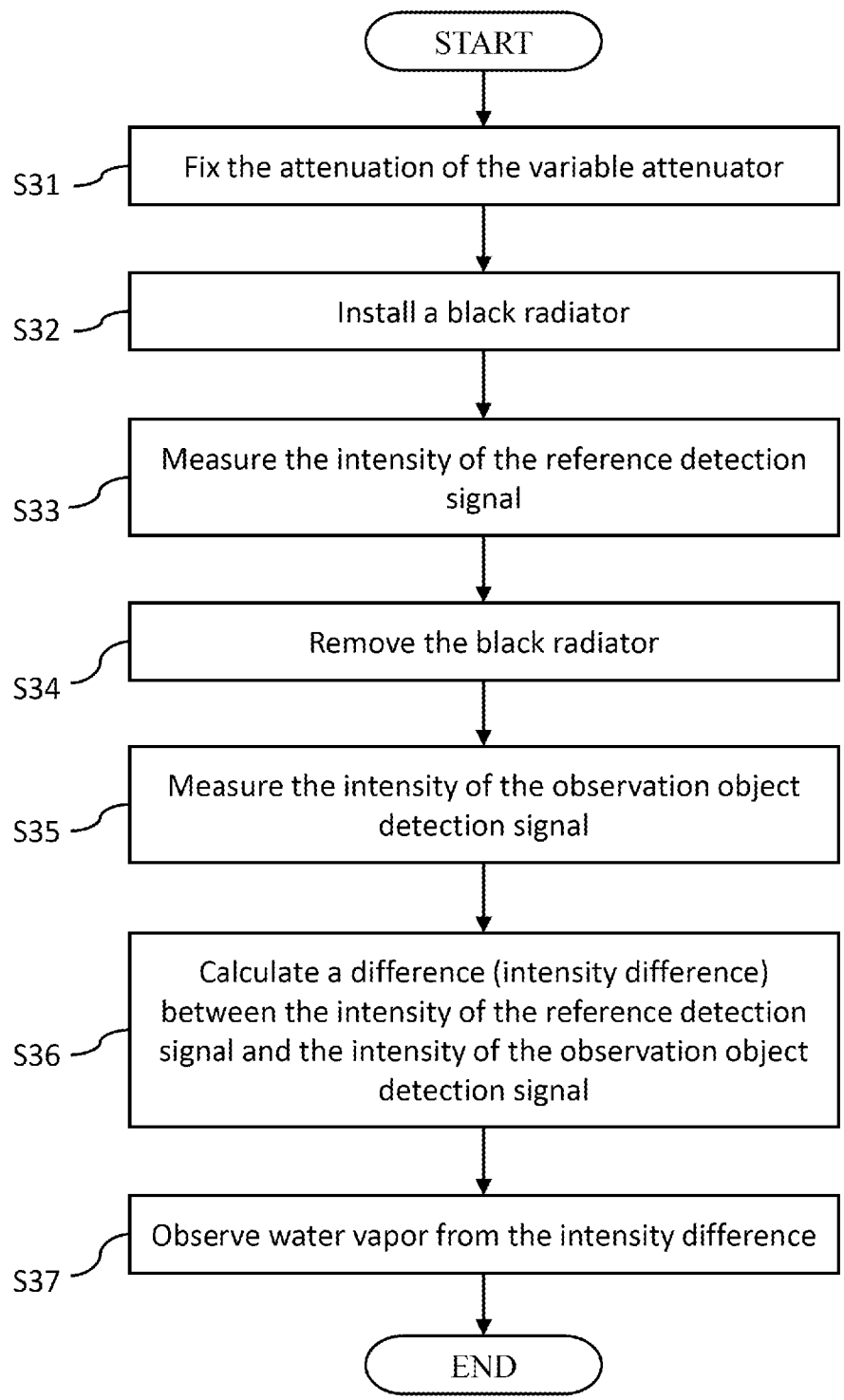
FIG. 6 is a flow chart illustrating an example of a specific method of generating observation data.

FIG. 6 is a flow chart showing an example of a specific method of generating an observation data. As shown in FIG. 6, the computing device fixes the attenuation of the variable attenuator 60 (S31). In this case, the attenuation amount is preferably as small as possible.

The blackbody 90 is installed on the receiving surface of the antenna ANT (S32). The arrangement of the blackbody 90 may be mechanically controlled by providing a moving mechanism for the blackbody 90 on the antenna ANT or manually.

The arithmetic module measures the intensity of the reference detection signal (S33).

The blackbody 90 is removed from the receiving surface of the antenna ANT (S34). The removal of the blackbody 90 may be mechanically controlled by providing a moving mechanism for the blackbody 90 on the antenna ANT, or may be performed manually.

The arithmetic module measures the intensity of the observation object detection signal (S35).

The arithmetic module calculates an intensity difference between the intensity of the reference detection signal and the intensity of the observation object detection signal (S36). The arithmetic module generates an observation data from the intensity difference, that is, observes water vapor (S37).

Figure 7:
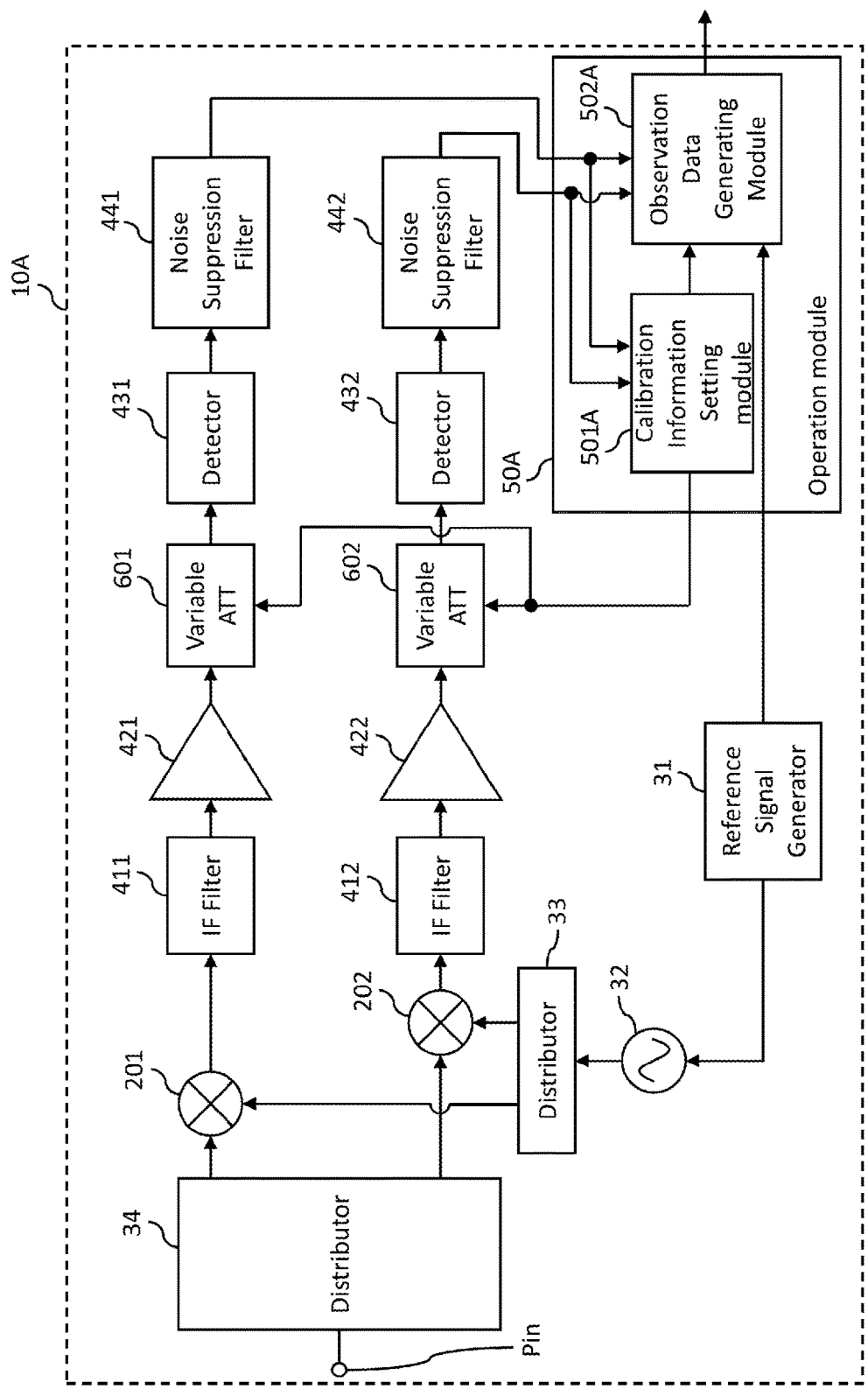
FIG. 7 is a block diagram showing a configuration of an observation device according to a second embodiment.

An observation technique according to a second embodiment of the present invention will be described with reference to the drawings. FIG. 7 is a block diagram showing a configuration of an observation device 10A according to a second embodiment.

As shown in FIG. 7, the observation device 10A according to the second embodiment differs from the observation device 10 according to the first embodiment in that the detection signals are measured in parallel by a plurality of circuits. In other respects, the configuration and processing of the observation device 10A are the same as those of the observation device 10, and the description of the same points is omitted.

As shown in FIG. 7, the observation device 10A includes a mixer 201, a mixer 202, the reference signal generator 31, the local signal generator 32, a distributor 33, a distributor 34, an IF filter 411, an IF filter 412, an amplifier 421, an amplifier 422, a detector 431, a detector 432, a noise suppression filter 441, a noise suppression filter 442, an operation module 50A, a variable attenuator (variable ATT) 601, and a variable attenuator (variable ATT) 602. The operation module 50A includes a calibration information setting module 501A and an observation data generating module 502A.

The distributor 33 and the distributor 34 are implemented by transmission lines of RF signals, such as waveguides.

The distributor 33 is connected to the local signal generator 32, the mixer 201, and the mixer 202. The distributor 34 is connected to the input terminal Pin, the mixer 201, and the mixer 202.

The mixer 201 is connected to the IF filter 411, and the IF filter 411 is connected to the amplifier 421. The amplifier 421 is connected to the variable attenuator 601, and the variable attenuator 601 is connected to the detector 431. The detector 431 is connected to the noise suppression filter 441, and the noise suppression filter 441 is connected to the operation module 50A.

The mixer 202 is connected to the IF filter 412, and the IF filter 412 is connected to the amplifier 422. The amplifier 422 is connected to the variable attenuator 602, and the variable attenuator 602 is connected to the detector 432. The detector 432 is connected to the noise suppression filter 442, and the noise suppression filter 442 is connected to the operation module 50A.

The mixer 201 and the mixer 202 have the same configuration as the mixer 20 described above.

The IF filter 411 and the IF filter 412 have the same configuration as the IF filter 41 described above except for the filter characteristics. The IF filter 411 has filter characteristics including a first intermediate frequency f(IF1) in a pass region and a second intermediate frequency f(IF2) in an attenuation region. The IF filter 412 has filter characteristics including the second intermediate frequency f(IF2) in a pass region and the first intermediate frequency f(IF1) in an attenuation region. The first intermediate frequency f(IF1) is set to a frequency obtained by subtracting the frequency of the RF signal from the frequency of the local signal. The second intermediate frequency f(IF2) is set to a frequency obtained by subtracting the frequency of the local signal from the frequency of the RF signal.

The variable attenuator 601 and the variable attenuator 602 have the same configuration as the variable attenuator 60 described above. A control signal is inputted to the variable attenuator 601 and the variable attenuator 602 from the calibration information setting module 501A.

The detector 431 and the detector 432 have the same configuration as the detector 43 described above. The noise suppression filter 441 and the noise suppression filter 442 have the same configuration as that of the noise suppression filter 44.

The local signal generator 32 generates a local signal of a predetermined frequency set by the reference signal. The frequency of the local signal is set to a frequency within a frequency band of a frequency spectrum used as the observation data.

The distributor 33 distributes the local signal and outputs it to the mixer 201 and the mixer 202. The distributor 34 distributes the RF signal and outputs it to the mixer 201 and the mixer 202.

The mixer 201 mixes the RF signal and the local signal and outputs a first IF signal. The mixer 202 mixes the RF signal and the local signal and outputs a second IF signal. The first IF signal and the second IF signal are the same signal.

The IF filter 411 performs filter processing on the first IF signal. The IF filter 412 performs filter processing on the second IF signal. As described above, the filter characteristics of the IF filter 411 and the filter characteristics of the IF filter 412 are different, and between the frequency components of the filtered first IF signal and the frequency components of the filtered second IF signal are different.

The amplifier 421 amplifies the filtered first IF signal. The amplifier 422 amplifies the filtered second IF signal.

The amplified first IF signal is inputted to the detector 431 via the variable attenuator 601. The amplified second IF signal is inputted to the detector 432 via the variable attenuator 602.

The detector 431 detects the amplified first IF signal and outputs a first detection signal. The detector 432 detects the amplified second IF signal and outputs a second detection signal. The noise suppression filter 441 suppresses a noise component of the first detection signal and outputs it to the operation module 50A. The noise suppression filter 442 suppresses a noise component of the second detection signal and outputs it to the operation module 50A.

The calibration information setting module 501A sets calibration information (calibration information) for a first detection signal by using a change of an intensity of the first detection signal acquired by changing the attenuation of the variable attenuator 601 in a state that the blackbody 90 is arranged on the antenna ANT. The calibration information setting module 501A sets calibration information (second calibration information) for the second detection signal by using a change in the intensity of the second detection signal acquired by changing the attenuation of the variable attenuator 602 in a state where the blackbody 90 is arranged on the antenna ANT. The calibration information setting module 501A outputs the calibration information to the observation data generating module 502A.

The observation data generating module 502A generates observation data by using a difference in the intensity of the first detection signal acquired in a state where the blackbody 90 is arranged on the antenna ANT and a state where the blackbody 90 is removed from the antenna ANT, and a difference in the intensity of the second detection signal acquired in a state where the blackbody 90 is arranged on the antenna ANT and a state where the blackbody 90 is removed from the antenna ANT. In this case, the observation data generating module 502A uses the first calibration information to calibrate the intensity difference of the first detection signal and uses the second calibration information to calibrate the intensity difference of the second detection signal.

As described above, even in a configuration including a plurality of circuits for measuring the detection signal, the observation device 10A can generate a high-precision observation data.

Further, in this configuration, detection signals for RF signals of two frequencies are obtained from local signals of one frequency. Accordingly, the observation device 10A obtains the predetermined number of frequency spectrum components by the half number of local signals. The observation device 10A obtains a frequency spectrum of a predetermined frequency band by a local signal in a frequency band narrower than the predetermined frequency band. Thus, the observation device 10A can generate an observation data composed of a frequency spectrum having the predetermined frequency band with simpler processing while narrowing a frequency band set as a local signal.

Figure 8:
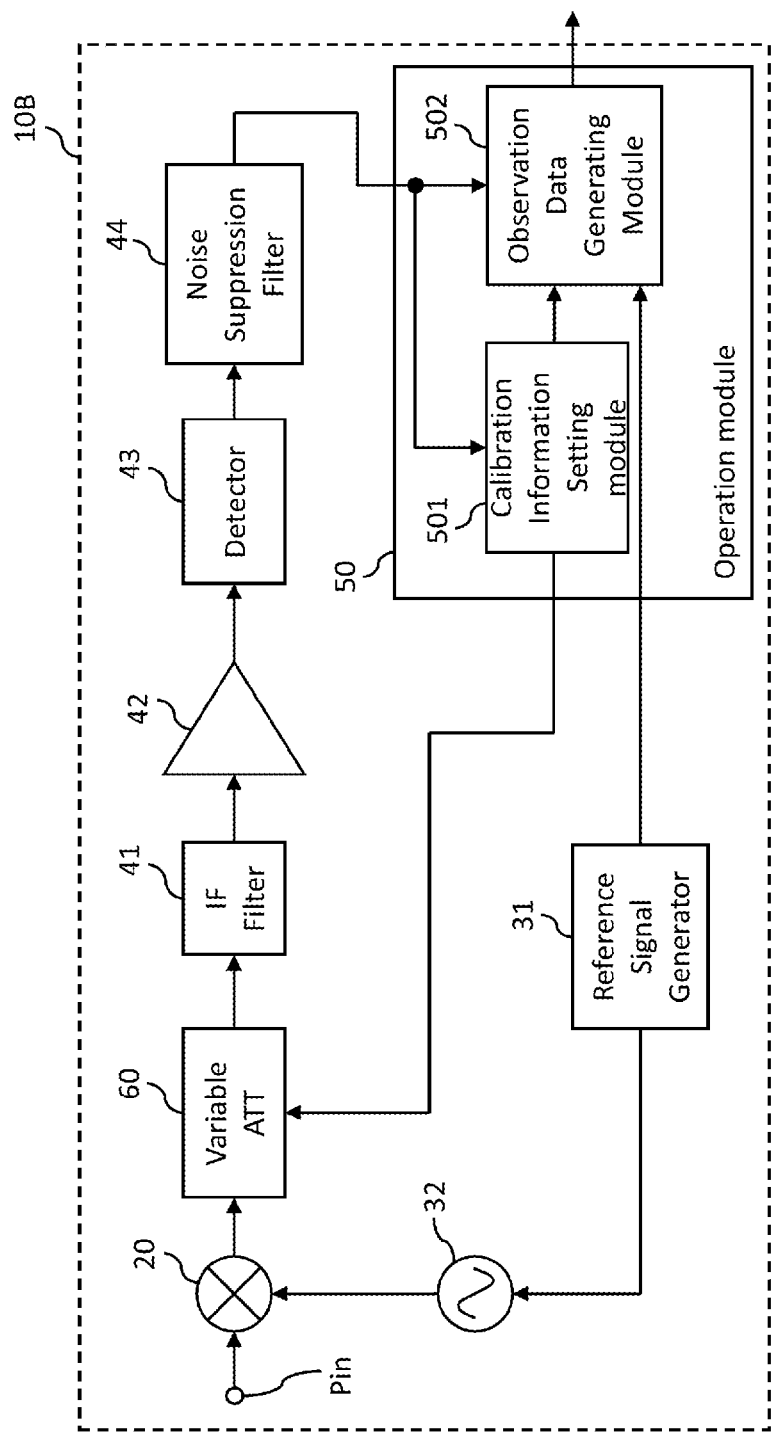
FIG. 8 is a block diagram showing a configuration of an observation device according to a third embodiment.

An observation technique according to a third embodiment of the present invention will be described with reference to the drawings. FIG. 8 is a block diagram showing a configuration of an observation device 10B according to a third embodiment.

As shown in FIG. 8, the observation device 10B according to the third embodiment differs from the observation device 10 according to the first embodiment in the arrangement position of the variable attenuator 60. The other components of the observation device 10B are the same as those of the observation device 10, and the description of the same parts will be omitted.

The variable attenuator 60 is connected between the mixer 20 and the IF filter 41. In this configuration, the calibration information setting module 501 can set calibration information capable of suppressing errors caused by the IF filter 41, errors caused by the amplifier 42, and errors caused by the detector 43.

Figure 9:
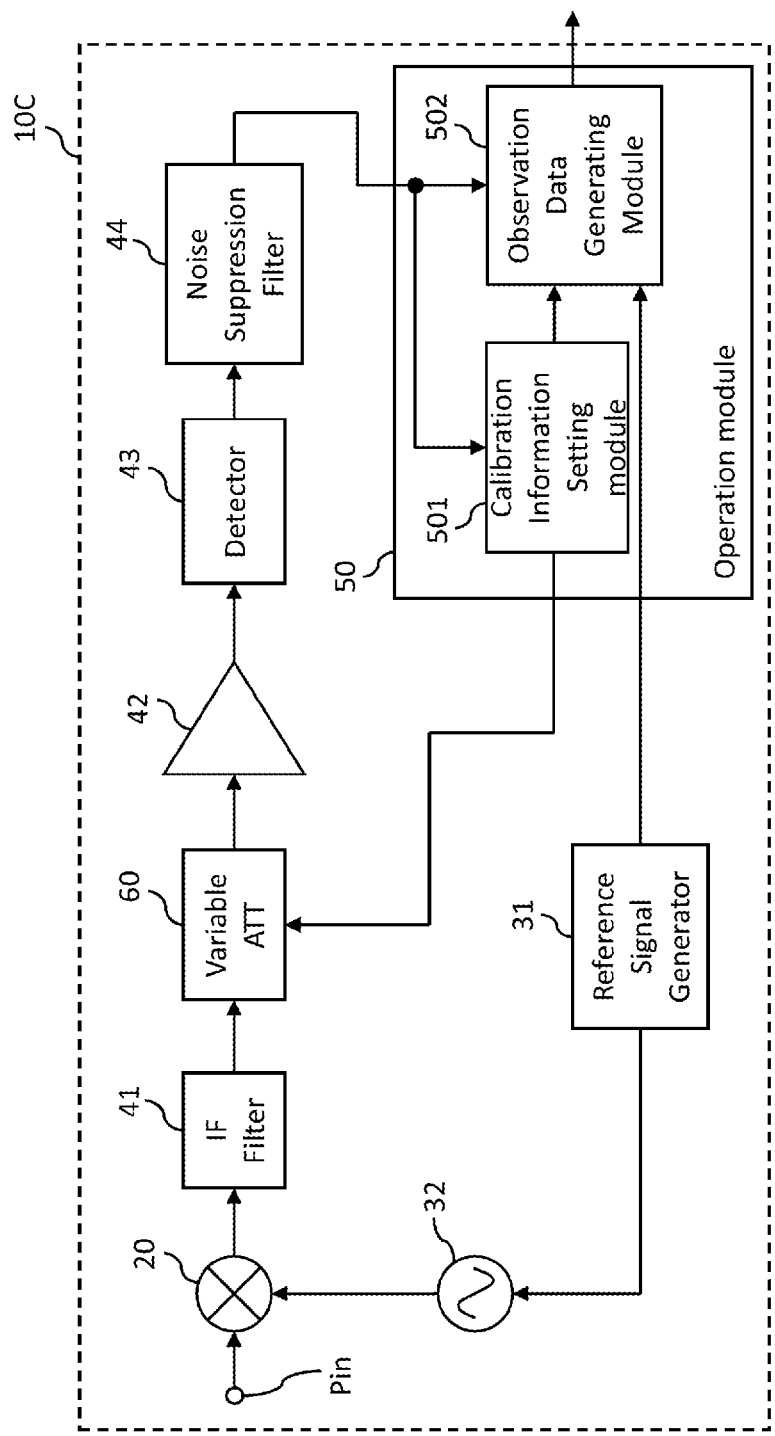
FIG. 9 is a block diagram showing a configuration of an observation device according to a fourth embodiment.

An observation technique according to a fourth embodiment of the present invention will be described with reference to the drawings. FIG. 9 is a block diagram showing a configuration of an observation device 10C according to a fourth embodiment.

As shown in FIG. 9, the observation device 10C according to the fourth embodiment differs from the observation device 10 according to the first embodiment in the arrangement position of the variable attenuator 60. The other components of the observation device 10C are the same as those of the observation device 10, and the description of the same parts will be omitted.

The variable attenuator 60 is connected between the IF filter 41 and the amplifier 42. In this configuration, the calibration information setting module 501 can set calibration information capable of suppressing an error caused by the amplifier 42 and an error caused by the detector 43.

The configuration of the observation device 10B according to the third embodiment and the configuration of the observation device 10C according to the fourth embodiment can also be applied to the observation device 10A according to the second embodiment, and effects corresponding to the respective combinations can be obtained.

[Terminology]

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processor. A processor can be a microprocessor, but in the alternative, the processor can be a controller, microcontroller, or state machine, combinations of the same, or the like. A processor can include electrical circuitry configured to process computer-executable instructions. In another embodiment, a processor includes an application specific integrated circuit (ASIC), a field programmable gate array (FPGA) or other programmable device that performs logic operations without processing computer-executable instructions. A processor can also be implemented as a combination of computing devices, e.g., a combination of a digital signal processor (DSP) and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C. The same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations).

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

For expository purposes, the term "horizontal" as used herein is defined as a plane parallel to the plane or surface of the floor of the area in which the system being described is used or the method being described is performed, regardless of its orientation. The term "floor" can be interchanged with the term "ground" or "water surface." The term "vertical" refers to a direction perpendicular to the horizontal as just defined. Terms such as "above," "below," "bottom," "top," "side," "higher," "lower," "upper," "over," and "under," are defined with respect to the horizontal plane.

As used herein, the terms "attached," "connected," "mated" and other such relational terms should be construed, unless otherwise noted, to include removable, moveable, fixed, adjustable, and/or releasable connections or attachments. The connections/attachments can include direct connections and/or connections having intermediate structure between the two components discussed.

Numbers preceded by a term such as "approximately," "about," and "substantially" as used herein include the recited numbers, and also represent an amount close to the stated amount that still performs a desired function or achieves a desired result. For example, the terms "approximately," "about," and "substantially" may refer to an amount that is within less than 10% of the stated amount. Features of embodiments disclosed herein preceded by a term such as "approximately," "about," and "substantially" as used herein represent the feature with some variability that still performs a desired function or achieves a desired result for that feature.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. An observation device, comprising:
   a mixer configured to mix a radio frequency (RF) signal and a local signal of an observation object, and to generate an intermediate frequency (IF) signal;
   a detector configured to detect the IF signal, and to generate a detection signal;
   a variable attenuator, connected between the mixer and the detector, configured to attenuate the IF signal; and
   a processing circuitry configured to set calibration information from a relationship between a change in a value of the variable attenuator and a change in an intensity of the detection signal.

2. The observation device according to claim 1, wherein the processing circuitry is further configured to generate observation data of the RF signal by using the intensity of the detection signal obtained in a state where the value of the variable attenuator is fixed and the calibration information.

3. The observation device according to claim 2, wherein the calibration information is set for each frequency of the IF signal.

4. The observation device according to claim 2, wherein the variable attenuator comprises:
   a first fixed resistance circuit and a second fixed resistance circuit, each using a plurality of resistance elements; and
   a variable impedance circuit using a semiconductor, wherein the variable impedance circuit is connected between the first fixed resistance circuit and the second fixed resistance circuit.

5. The observation device according to claim 3, wherein the variable attenuator comprises:
   a first fixed resistance circuit and a second fixed resistance circuit, each using a plurality of resistance elements; and
   a variable impedance circuit using a semiconductor, wherein the variable impedance circuit is connected between the first fixed resistance circuit and the second fixed resistance circuit.

6. The observation device according to claim 2, further comprising:
   an IF filter connected between the mixer and the detector; and
   an amplifier connected between the IF filter and the detector, wherein
   the variable attenuator is located between the mixer and the amplifier.

7. The observation device according to claim 5, further comprising:
   an IF filter connected between the mixer and the detector; and
   an amplifier connected between the IF filter and the detector, wherein
   the variable attenuator is located between the mixer and the amplifier.

8. The observation device according to claim 2, wherein
   the RF signal of the observation object is generated by electromagnetic waves radiated from a blackbody and water vapor, and
   the observation data is a difference between the intensity of the RF signal due to the electromagnetic wave radiated from the blackbody and the intensity of the RF signal due to the electromagnetic wave radiated from the water vapor.

9. The observation device according to claim 7, wherein
   the RF signal of the observation object is generated by electromagnetic waves radiated from a blackbody and water vapor, and
   the observation data is a difference between the intensity of the RF signal due to the electromagnetic wave radiated from the blackbody and the intensity of the RF signal due to the electromagnetic wave radiated from the water vapor.

10. A method, comprising:
    mixing a radio frequency (RF) signal and a local signal of an observation object to generate an intermediate frequency (IF) signal;
    detecting the IF signal to generate a detection signal; and
    setting calibration information from a relationship between a change in attenuation with respect to the IF signal and a change in intensity of the detection signal.

11. The method according to claim 10, further comprising:
    generating observation data of the RF signal by using the intensity of the detection signal obtained in a state where the attenuation is fixed and the calibration information.

12. A non-transitory computer-readable medium having stored thereon computer-executable instructions which, when executed by a computer, cause the computer to:
    mix a radio frequency (RF) signal and a local signal of an observation object to generate an intermediate frequency (IF) signal;
    detect the IF signal to generate a detection signal; and
    set calibration information from a relationship between a change in attenuation of the IF signal and a change in intensity of the detection signal.

13. The non-transitory computer-readable medium according to claim 12, further causing the computer to:
    generate observation data of the RF signal by using the intensity of the detection signal obtained in a state where the attenuation is fixed and the calibration information.

* * * * *